(12) United States Patent
Rensen et al.

(10) Patent No.: US 10,791,932 B2
(45) Date of Patent: Oct. 6, 2020

(54) OPTICAL DETECTION METHOD AND DEVICE FOR OPTICAL DETECTION OF THE CONDITION OF JOINTS

(75) Inventors: Wouter Harry Jacinth Rensen, Eindhoven (NL); Michael Cornelis Van Beek, Eindhoven (NL); Rik Harbers, Zurich (CH)

(73) Assignee: Demcon Hemics B.V., Enschede (NL)

( * ) Notice: Subject to any disclaimer, the term of this patent is extended or adjusted under 35 U.S.C. 154(b) by 160 days.

(21) Appl. No.: 12/992,609

(22) PCT Filed: May 20, 2009

(86) PCT No.: PCT/IB2009/052112
§ 371 (c)(1),
(2), (4) Date: Nov. 15, 2010

(87) PCT Pub. No.: WO2009/147560
PCT Pub. Date: Dec. 10, 2009

(65) Prior Publication Data
US 2011/0066034 A1    Mar. 17, 2011

(30) Foreign Application Priority Data
May 26, 2008  (EP) .................................... 08156917

(51) Int. Cl.
*A61B 5/00* (2006.01)
*A61B 5/02* (2006.01)

(52) U.S. Cl.
CPC ........ *A61B 5/0059* (2013.01); *A61B 5/02007* (2013.01); *A61B 5/4528* (2013.01); *A61B 5/6826* (2013.01); *A61B 5/6838* (2013.01)

(58) Field of Classification Search
CPC . A61B 5/0059; A61B 5/02007; A61B 5/6838; A61B 5/6826; A61B 5/4528
See application file for complete search history.

(56) References Cited

U.S. PATENT DOCUMENTS

| | | | | |
|---|---|---|---|---|
| 5,038,039 A | * | 8/1991 | Wong et al. | 250/339.12 |
| 5,473,160 A | * | 12/1995 | Eysel et al. | 250/339.12 |
| 5,560,351 A | * | 10/1996 | Gravenstein et al. | 128/200.26 |
| 6,070,093 A | * | 5/2000 | Oosta et al. | 600/316 |
| 6,161,537 A | * | 12/2000 | Gravenstein et al. | 128/200.26 |
| 6,172,743 B1 | * | 1/2001 | Kley et al. | 356/39 |

(Continued)

FOREIGN PATENT DOCUMENTS

| | | |
|---|---|---|
| DE | WO199904683 | 4/1999 |
| WO | WO2007000349 | 4/2007 |

*Primary Examiner* — Bo Joseph Peng
(74) *Attorney, Agent, or Firm* — Saile Ackerman LLC; Stephen B. Ackerman; Rosemary L. S. Pike

(57) ABSTRACT

An optical detection method is provided, wherein a body part (5) comprising at least one joint is irradiated with light. Local attenuation of the light by the body part (5) is detected as attenuation measurements (2) at the position of the at least one joint and at the position of at least one other portion of the body part (5); and wherein blood flow to and/or from the body part (5) is temporarily at least partially blocked and thereafter enabled again (3). Distinct local attenuation measurements for the at least one joint and for at least one other portion of the body part (5) are performed for at least two of the times before (I), during (II), and after (III) the blocking of blood flow.

5 Claims, 4 Drawing Sheets

(56) References Cited

U.S. PATENT DOCUMENTS

| | | | |
|---|---|---|---|
| 6,222,189 B1* | 4/2001 | Misner et al. | 250/341.1 |
| 6,424,859 B2* | 7/2002 | Jackson et al. | 600/475 |
| 6,587,704 B1* | 7/2003 | Fine et al. | 600/335 |
| 6,763,256 B2* | 7/2004 | Kimball et al. | 600/336 |
| 6,816,266 B2* | 11/2004 | Varshneya et al. | 356/477 |
| 6,879,850 B2* | 4/2005 | Kimball | 600/336 |
| 6,953,435 B2* | 10/2005 | Kondo et al. | 600/485 |
| 7,280,860 B2* | 10/2007 | Ikeda et al. | 600/344 |
| 2001/0037811 A1* | 11/2001 | Beuthan et al. | 128/897 |
| 2003/0095263 A1* | 5/2003 | Varshneya et al. | 356/477 |
| 2003/0109791 A1* | 6/2003 | Kondo et al. | 600/500 |
| 2004/0034293 A1* | 2/2004 | Kimball | 600/323 |
| 2004/0034294 A1* | 2/2004 | Kimball et al. | 600/323 |
| 2004/0162471 A1* | 8/2004 | Ikeda et al. | 600/322 |
| 2006/0063995 A1* | 3/2006 | Yodh et al. | 600/323 |
| 2006/0217615 A1* | 9/2006 | Huiku | A61B 5/08 600/484 |
| 2007/0088205 A1 | 4/2007 | Hull et al. | |
| 2007/0208395 A1* | 9/2007 | Leclerc et al. | 607/86 |
| 2007/0265533 A1* | 11/2007 | Tran | A61B 5/021 600/481 |

* cited by examiner

OPTICAL DETECTION METHOD AND DEVICE FOR OPTICAL DETECTION OF THE CONDITION OF JOINTS

FIELD OF INVENTION

The present invention relates to an optical detection method and to a device for optical detection of the condition of joints.

BACKGROUND OF THE INVENTION

In the context of the present application, the term light is to be understood to mean non-ionizing electromagnetic radiation, in particular with wavelengths in the range between 400 nm and 1400 nm. The term body part means a part of a human or animal body. The term blocking covers both complete blocking and blocking to a substantial extent.

In general, the present invention relates to optical detection of joint conditions, in particular to the optical detection of joint diseases such as rheumatoid arthritis (RA). The treatment of such joint diseases is staged. Usually, a patient first receives pain killers. These are frequently followed by non-steroid anti-inflammatory drugs (NSAIDs) and disease modifying anti-rheumatic drugs (DMARDs). In many cases, the last stage in treatment with drugs is the use of biological therapies. In particular the last category is expensive and treatment can cost tens of thousands of dollars per year per patient. Additionally, the drugs used in later stages of treatment often cause more severe side effects. With respect to such joint diseases, medical professionals base their decisions on changes in therapy on disease activity which is given by the number and the severity of inflamed joints.

Since rheumatoid arthritis is a progressive disease and early diagnosis and start of treatment can help postponing adverse effects and high costs of treatment, there is a demand for methods and devices for providing satisfactory information about the condition of joints and which assist a medical professional to come to a conclusion with respect to the actual joint condition.

It has been found in time-dependent measurements using non-targeted fluorescent dyes administered to the patient that perfusion dynamics in diseased joints are different as compared to normal healthy joints. However, in the clinical practice of rheumatologists, administration of contrast agents is impractical in most cases.

As an alternative, it has been proposed to use Diffuse Optical Tomography (DOT) to image joints for providing information about their condition. In a research project, venous blood flow to a body part has been temporarily obstructed by means of a pressure cuff and a single joint has been imaged by means of DOT. In such studies, it has been found that optical parameters exist which correlate with the presence of rheumatoid arthritis (RA).

For example, it is known that inflammation can be recognized by a change in perfusion. Blood constituents, in particular both oxygenated and deoxygenated hemoglobin have distinct optical characteristics compared to other constituents of the human or animal body and thus can in principle be optically detected.

U.S. Pat. No. 6,424,859 B2 discloses a near infrared spectroscopic technique for characterizing the condition of a joint. The results from a spectroscopic measurement are compared to a database in which measurement results for a plurality of arthritic and healthy joints are stored. However, this technique does not allow satisfactorily separating signals resulting from blood and signals from other sources in the body. Further, the technique does not allow separating joint-specific features from features resulting from tissue such as skin, fat, etc.

Currently there is no satisfactory tool helping medical professionals in early detection of joint diseases or, more specifically, in quantitative and objective detection of inflamed joints. The same holds for monitoring of disease activity, there is no tool for fast, objective and quantitative detection of disease activity (the degree of inflammation of joints).

SUMMARY OF THE INVENTION

It is an object of the present invention to provide an optical detection method and a device for optical detection of the condition of joints which provide information about the condition of joints allowing an early detection of joint diseases and allowing monitoring disease activity. The optical detection method and the device for optical detection of the condition of joints shall provide sufficient information to assist a medical professional to come to a conclusion with respect to the joint condition and disease activity, respectively.

The object is solved by an optical detection method according to claim 1. In the optical detection method, a body part comprising at least one joint is irradiated with light and local attenuation of the light by the body part is detected as attenuation measurements at the position of the at least one joint and at the position of at least one other portion of the body part. Blood flow to and/or from the body part is temporarily at least partially blocked and thereafter enabled again. Distinct local attenuation measurements for the at least one joint and for the at least one other portion of the body part are performed for at least two of the times before, during, and after the blocking of blood flow. Measurements before and after the blocking of the blood flow can give relevant data, if only because it can take the body a remarkable long time (>5 minutes) to fully recover and return to the same transmission properties as before the measurement. Since the attenuation of the light used for irradiation is locally detected for two distinct positions of which at least one is a joint, differences in the optical properties of the at least one joint compared to the at least one other portion of the body part can be detected. Since the distinct local attenuation measurements are performed before and during the blocking of blood flow, before and after the blocking of blood flow, and/or during and after the blocking of blood flow, the response of the at least one joint to changes in blood flow compared to the at least one other portion can be detected. During inflammation of a joint, the number and properties of blood vessels (capillaries) in the joint change. This effect together with the specific light absorption of blood is used for measuring the condition of a joint. Due to the measurements under different blood flow conditions, the signal resulting from blood can be separated from signals resulting from other sources of light attenuation in the body. Since at least one joint and at least one other body portion of the body part (e.g. next to the joint) are measured, joint-specific results are achieved and contributions from tissues which are present in both the joint and the other body portion (such as fat, skin, etc.) can be separated. As a result, a signal which is joint-specific for changes in blood content can be obtained. Separate measurements to identify the composition (e.g. bone, fat, skin, etc.) of the body part can be omitted. As a consequence, valuable information about the joint condition and/or disease activity is provided to a medical professional. It should be noted that no complete blocking of the blood flow is required but a significant partial reduction in blood flow may suffice.

Preferably, the distinct local attenuation measurements for the at least one joint and for the at least one other portion of the body part are performed at all three intervals before, during, and after the blocking of blood flow. In this case, even more information about the condition the at least one joint is provided.

If the at least one other portion of the body part is another joint, the response of different joints to changes in blood flow can be compared and information about differences in the condition of several joints is provided.

Preferably, for the at least one joint and the at least one other portion of the body part, continuous distinct local attenuation measurements are performed before the blocking of blood flow, during the blocking of blood flow, and after the blocking of blood flow. In this case, due to the continuous measurements, exact information about the time point of a response to a change in blood flow is provided for the at least one joint and the at least one other portion.

If the results of distinct local attenuation measurements for the at least one joint and for the at least one other portion of the body part which are acquired substantially simultaneously are compared to each other, the differences in response between the at least one joint and the at least one other portion are provided in an advantageous way.

Preferably, the blood flow is blocked by application of pressure. Thus, a simple and convenient way for obstructing the blood flow is provided.

According to an aspect, during acquisition of the distinct local attenuation measurements, the body part is immersed in an optically matching medium. In this case, optical boundary effects and the dynamic range of intensities to which a detector is subjected are reduced.

The object is further solved by a device for optical detection of the condition of joints according to claim 8. The device comprises: a measurement unit for irradiating a body part comprising at least one joint with light and locally detecting attenuation of the light at the at least one joint and at least one other portion of the body part; a blood flow blocking unit for blocking the blood flow to and/or from the body part; and a control unit. The control unit controls the device such that: blood flow to and/or from the body part is temporarily at least partially blocked and thereafter enabled again; and distinct local attenuation measurements for the at least one joint and for at least one other portion of the body part are performed for at least two of the times before, during, and after the blocking of blood flow. The device achieves the advantages described above with respect to the method.

If the blood flow blocking unit is adapted to block the blood flow by application of pressure, the advantages can be realized in a simple and convenient way.

If the measurement unit comprises a light source unit capable of emitting light of at least two distinct wavelengths, one wavelength can be chosen such that blood has a high absorption and another wavelength can be chosen such that the absorption of blood is low or comparable to surrounding tissue. Thus, more detailed information about perfusion of the at least one joint and the at least one other portion of the body part are provided and can be analyzed for judging the condition of the at least one joint.

Preferably, the light source unit comprises at least two lasers. In this case, well defined wavelengths are provided and differences in perfusion can be detected with high accuracy.

Preferably, the device is a medical optical detection device.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

Figure 1:
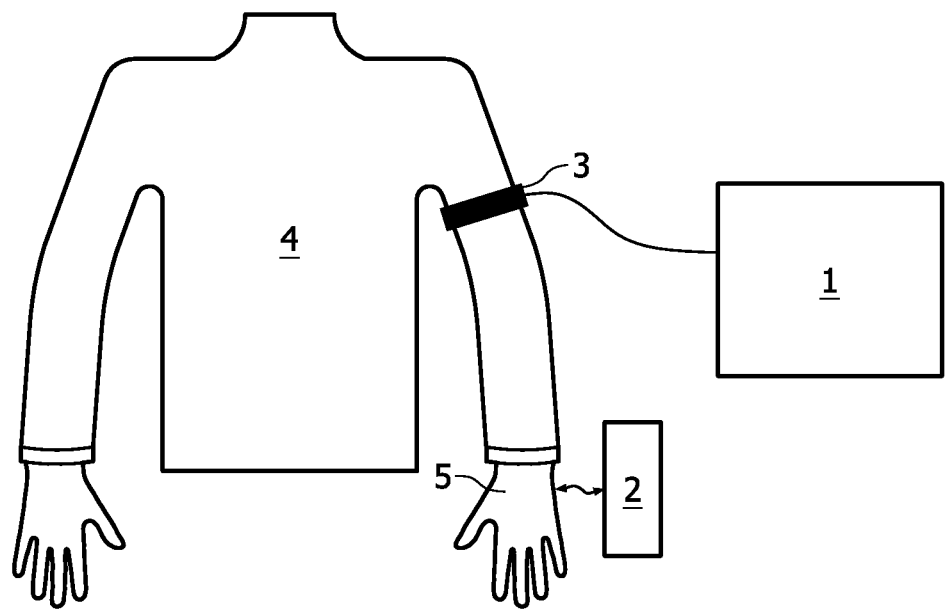
FIG. 1 schematically shows a set-up for optical detection of the condition of joints according to an embodiment.

An embodiment of the present invention will now be described with reference to the figures. FIG. 1 schematically shows a set-up for the optical detection of the condition of joints. In the illustration, a human body 4 is schematically shown as a body and a hand forms the body part 5 to be examined. However, it should be noted that the invention is not restricted to human bodies and e.g. animal bodies may be subjected to examination. Further, the body part 5 is not restricted to a hand but may also be formed by another body part comprising at least one joint 6 such as arms, legs, feet, etc.

In the embodiment shown, the device for optical detection of the condition of joints comprises a measurement unit 2, a blood flow blocking unit 3, and a control unit 1. The control unit; that is, a processor, 1 is provided to control the operation of the device and data acquisition. The measurement unit 2 is provided to irradiate portions of the body part 5 under examination with light and measure the local attenuation of the light at different positions of the body part 5. For example, in the embodiment shown the measurement unit 2 is formed by a measurement head which will be described in more detail below. The blood flow blocking unit 3 is provided for temporarily blocking the blood flow to and/or from the body part 5 under examination. In the embodiment, the blood flow blocking unit 3 is provided by a pressure cuff surrounding the arm to which the hand under examination belongs and obstructing the blood flow by application of pressure to the upper arm. It should be noted that the blood flow blocking unit 3 may be adapted differently in order to allow temporarily at least partially blocking the blood flow to and/or from body parts 5 other than a hand.

The construction of the measurement unit 2 according to the embodiment will be described in further detail with reference to FIG. 2.

Figure 2:
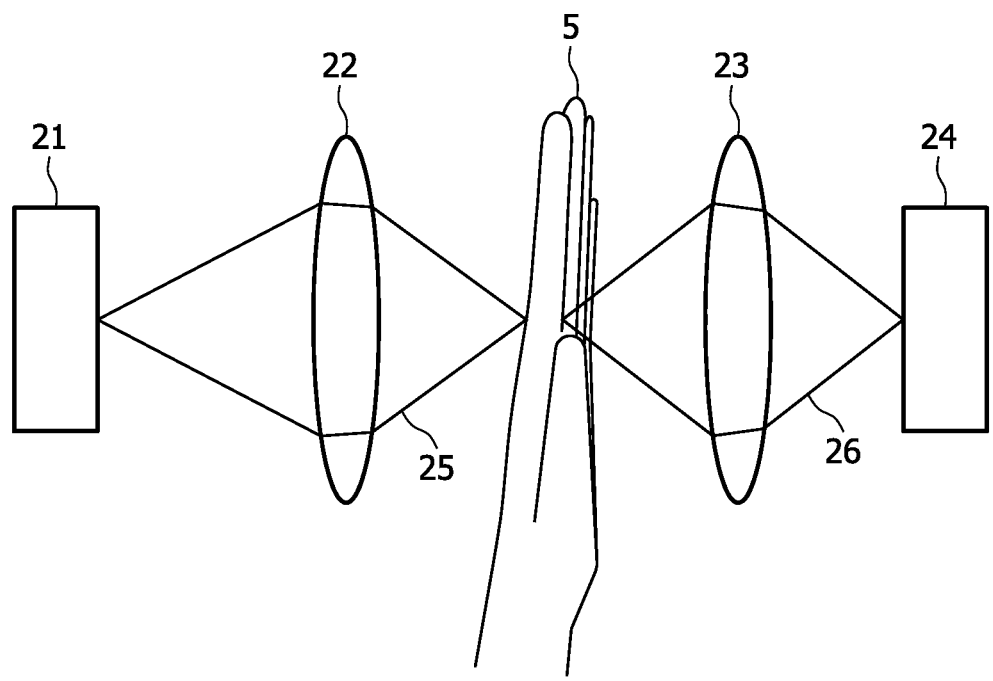
FIG. 2 schematically shows details of a measurement unit according to an embodiment.

The measurement unit 2 schematically shown in FIG. 2 is adapted for attenuation measurements in transmission geometry. The measurement unit 2 comprises a light source unit 21 emitting a beam of light for irradiating the body part 5. The light source unit 21 comprises at least one light source and appropriate light guides to direct the beam of light to the body part 5. The light source may be formed by a lamp or by one or more lasers and the light guides may for instance be formed by optical fibers. The light source unit 21 is adapted to be capable to emit light of at least two different wavelengths, preferably in the red to near infrared, wherein one wavelength is chosen such that blood has a high absorption and another wavelength is chosen such that the absorption of blood is low or comparable to surrounding tissue. Suitable wavelengths are for instance 600 nm and 805 nm but other wavelengths fulfilling these criteria are possible as well. Wavelengths in the wavelength range between 550 and 980 nm are particularly suitable. Further, an optical component 22 which e.g. may be formed by a lens is provided for directing the light to the body part 5. The optical component 22 is capable of concentrating the light (irradiation light 25) on a specific area of interest (or several specific areas of interest; i.e. specific positions) of the body part 5 as will be described below. A second optical element 23 is provided to collect light emerging from the specific area (or areas) of interest and direct the collected light 26 to a detection element 24. The detection element 24 may for instance be formed by a photodiode, a CCD, an optical guide such as a fiber connecting to a photodiode, or another light detection scheme known in the art.

The measurement unit 2 is adapted such that distinct local attenuation measurements for at least two different portions of the body part 5 can be performed.

The control unit 1 is adapted such that it controls at least partial blocking of the blood flow to and/or from the body part 5 by means of the blood flow blocking unit 3. Further, it controls the measurement unit 2 such that local attenuation measurements are performed before the blood flow is blocked (interval I in FIG. 4), local attenuation measurements (at the same positions) are performed during the blocking of blood flow (interval II in FIG. 4), and local attenuation measurements (at the same positions) are performed after restoring the blood flow (interval III in FIG. 4).

Figure 4:
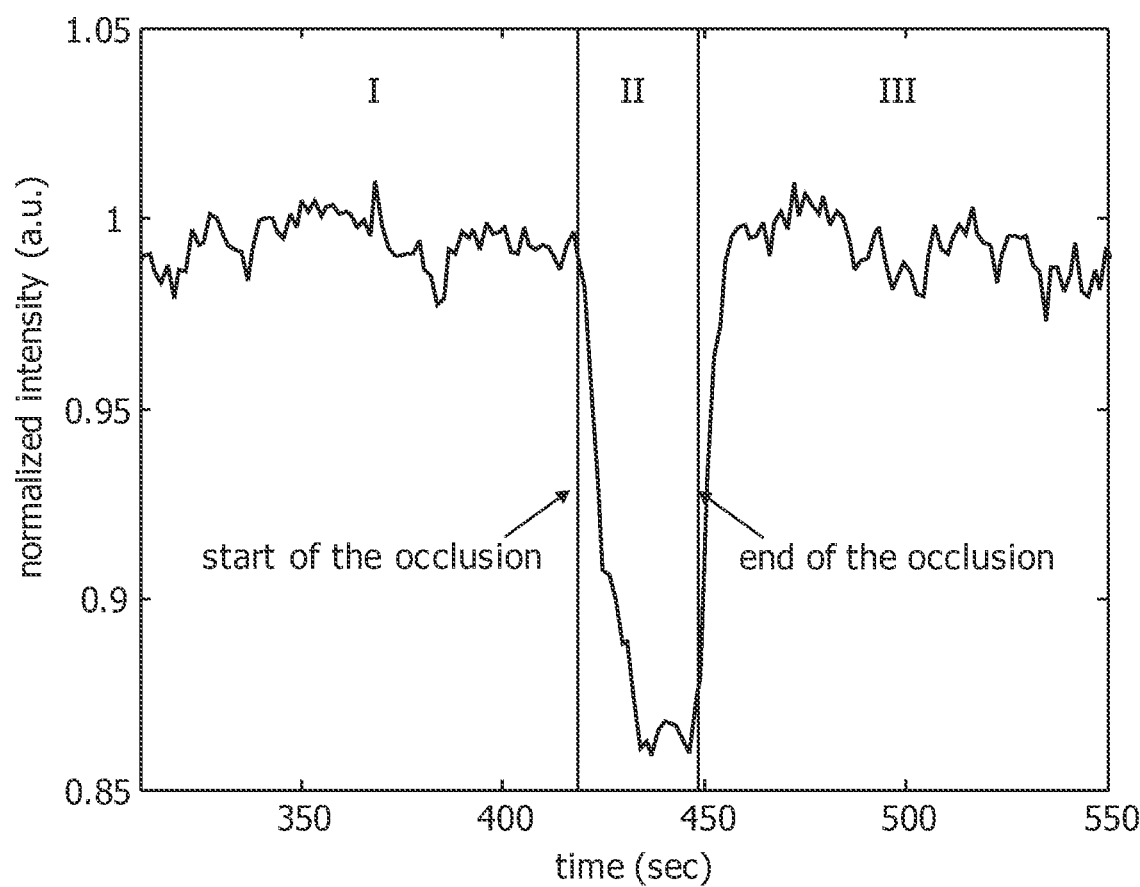
FIG. 4 shows an example for an attenuation measurement as a function of time.

FIG. 4 shows an example of attenuation measurements (optical intensity measurements) over time on a finger joint as a particular area of interest before the blocking of blood flow (I), during the blocking of blood flow (II; "occlusion"), and after the blocking of blood flow (III). It can be seen that the attenuation measurements in the three time intervals (before (I), during (II), and after (III) occlusion) are performed continuously to achieve time-resolved measurements. It can be seen that the measured intensity drops after blocking the blood flow and rises again after restoring of the blood flow. However, the height of the drop and the time relation between the blocking/restoring of blood flow and change in the measured intensity provide important information about the condition of the joint 6 under examination.

According to the invention attenuation measurements are not only performed for a single joint 6 but at least one joint and at least one other portion of the body part under examination are measured simultaneously, i.e. within the same cycle of normal blood flow (I), obstruction of blood flow (II), and restoration of the blood flow (III). This is achieved by simultaneously performing distinct local attenuation measurements at the position of the at least one joint 6 and at the position of the at least one other portion of the body part 5. The at least one other portion of the body part may be another joint or a portion which is not a joint and serves as a reference portion. For each of the positions, attenuation measurements are performed for the at least two different wavelengths of the irradiation light for one of which blood has a high absorption and for the other one of which absorption of blood is low or comparable to surrounding tissue. Preferably, attenuation measurements for multiple joints of a patient are performed simultaneously. In the preferred embodiment, all joints in both hands are measured simultaneously.

As a result, the following steps are performed according to the embodiment: distinct local attenuation measurements for at least one joint and at least one other portion of the body part 5 are performed; the blood flow to the body part 5 under examination is temporarily blocked by means of the blood flow blocking unit 3 and distinct local attenuation measurements for the at least one joint and the at least one other portion are performed; and the blood flow is restored and distinct local attenuation measurements for the at least one joint and the at least one other portion of the body part 5 are performed. In each of the intervals, several attenuation measurements are performed to achieve a time-resolved measurement. Further, the time dependent behavior of the at least one joint and the at least one other portion of the body part 5 are analyzed by the processor both independently and with respect to each other. Exploiting the measurements for at least two different wavelengths allows analyzing the perfusion dynamics and oxygenation.

Figure 3:
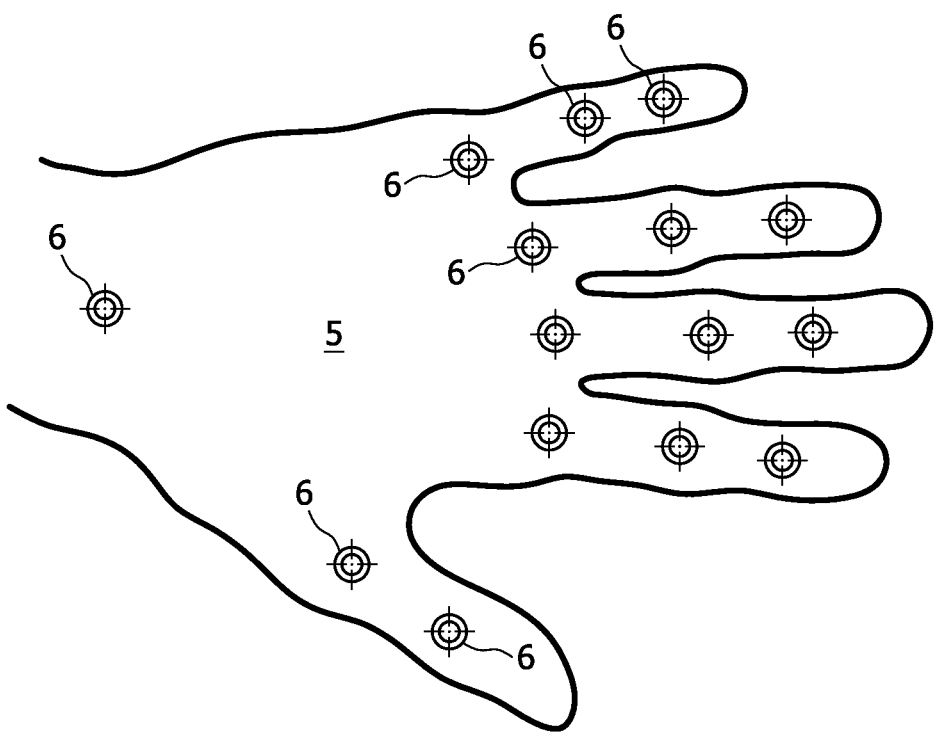
FIG. 3 schematically shows a human hand as an example for a body part with the positions of joints indicated.

Preferably, multiple joints are measured simultaneously and the time dependent behavior of these multiple joints with respect to each other is analyzed. Still more preferably, all joints of a body part 5 are measured simultaneously. FIG. 3 shows a hand as an example for a body part 5 to be examined and the positions of joints 6 are indicated by crosshairs (it should be noted that not all joints are provided with reference signs). The indicated positions can be used as positions for the local attenuation measurements and additionally positions between these indicated positions can be used for reference attenuation measurements.

In the embodiment shown in FIG. 1, via the measurement unit 2, the control unit 1 detects the spectral characteristics of the body part 5 containing joints 6. After a baseline measurement, the blood flow is (at least partially) blocked by the blood flow blocking unit 3. The measurement unit 2 now detects spectral changes related to the reduced blood flow. After some time, e.g. 30 seconds, the blood flow is restored by operating the blood flow blocking unit 3 appropriately (e.g. releasing the pressure cuff). The measurement unit 2 detects how fast the perfusion is restored in the joints and in which order the perfusion is restored. Preferably, the perfusion recovery is also compared between joints and other areas of the body part 5. Inflamed joints will have a different perfusion and oxygenation as compared to healthy joints. As a result, the dynamic spectral behavior which is measured by the measurement unit 2 will be different.

Figure 5:
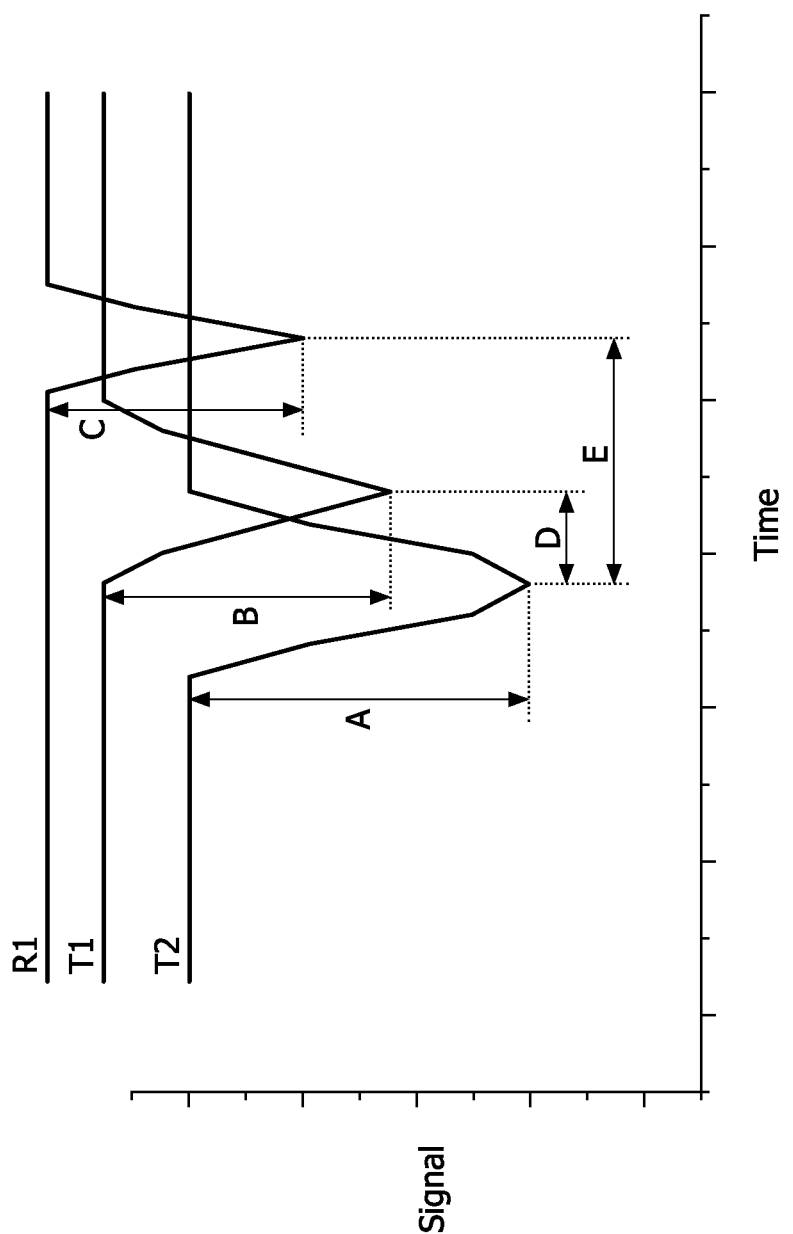
FIG. 5 schematically illustrates the results of simultaneous distinct local attenuation measurements for two joints and one other portion of the body part which is not a joint.

FIG. 5 shows an example for the results of attenuation measurements (in transmission geometry) performed simultaneously. The trace marked with T1 corresponds to local attenuation measurements at a first joint, the trace marked with T2 corresponds to local attenuation measurements at a second joint, and the trace marked with R1 corresponds to local attenuation measurements at a reference position which is not a joint. The characteristics A, B, C of the drops occurring in the traces can be different. Thus, a single drop can be analyzed and also the relation between the drops A, B, C in the different traces T1, T2, and R1. Inflamed joints can show signs of high perfusion such as an increased drop in transmission compared to other joints or compared to a reference position. Also the time differences D, E between the changes in transmission between the traces T1, T2, and R1 can be used as marker for inflammation and provide important information.

The time-dependent behavior of individual joints, the behavior of joints with respect to each other and with respect to other parts (that can act as a reference) is analyzed.

In the embodiment described above, the measurement unit 2 has been adapted for measurements in transmission geometry, i.e. the body part is irradiated from one side and the light having passed through the body part is measured on the opposite side. In a modification of the embodiment, the measurement unit 2 can be adapted for attenuation measurements in reflection geometry. In this case, irradiation and detection are performed from the same side of the body part 5. In reflection geometry, the optical components 22 and 23 can be combined. It is advantageous to separate the diffuse reflected light from the illumination light. This can be achieved e.g. by orthogonal polarized spectral imaging (OPSI) or darkfield imaging or other suitable techniques known in the art.

It should be noted that, in the embodiments, the blood flow need not be completely blocked but a substantial reduction of the blood flow may suffice.

A plurality of different ways for implementing the measurement unit 2 exists. It is an essential feature that the local collection of light from multiple portions of the body part 5 under examination is measured. This can e.g. be achieved by illuminating a single spot at a time and detecting a corresponding single spot on the body part 5 and scanning the position of the illumination and detection spot over the body part 5.

A further, more preferred possibility is to illuminate the whole body part 5 and to image the transmitted (or reflected) light with a CCD camera or another suitable camera. However, due to the diffuse transmission, in this case the resolution of the image is limited and light traveling e.g. between fingers may overload the detector.

A still more preferred possibility is to illuminate a discrete number of spots on the body part 5. This implementation has the advantage that less stray light reaches the detector which leads to a higher resolution and that the intensity of all the spots can be adjusted such that only a limited dynamic range is required for the detector.

It is also possible to immerse the body part 5 under examination in an optically matching medium, e.g. a fluid, in order to reduce optical boundary effects and the dynamic range of intensities falling on the detector. In such a technique, a fluid having optical properties (such as the optical absorption coefficient and the reduced scattering coefficient) similar to those of tissue is employed.

Further, to detect different wavelengths, it is possible to alternate the illumination wavelength. It is also possible to illuminate with all required wavelengths simultaneously and separate the different wavelengths in the detection path, e.g. using filters or a spectrograph.

In a preferred implementation, multiple body parts (e.g. both hands) are measured simultaneously.

Although it has been described with respect to the embodiment that at least two wavelengths are used for illumination, the invention is not restricted to that. For example, a larger number of discrete wavelengths can be used or even a complete spectrum over a certain range of wavelengths (e.g. 650 to 1000 nm). However, acquiring a complete spectrum requires more costly components as compared to a few distinct wavelengths. If several types of tissue components (such as fat, water, etc.) shall be discriminated, it might be advantageous to use more than two distinct wavelengths. Using more wavelengths helps improving the accuracy of the device, however, at increased cost and complexity.

The invention claimed is:

1. Optical detection method of a condition of a joint, the method comprising:
    irradiating a body part comprising at least one joint with light using a light source unit comprising at least one light source; simultaneously detecting local attenuation of the light by the body part as attenuation measurement at the position of the at least one joint and local attenuation of light by the body part as an attenuation measurement at the position of at least one other portion of the body part, using a light detection element, wherein the at least one other portion of the body part is a reference position which is not a joint; and reducing blood flow to and/or from the body part by a pressure cuff and thereafter restoring blood flow to and/or from the body part; wherein distinct local attenuation measurements for the at least one joint and for the at least one other portion of the body part are simultaneously performed at least two of: before the reducing of blood flow (I), during the reducing of blood flow (II), and after the reducing of blood flow (III); wherein the method further comprises comparing results of the distinct local attenuation measurements for the at least one joint and for the at least one other portion of the body part to each other.

2. Optical detection method according to claim 1, wherein the distinct local attenuation measurements for the at least one joint and for the at least one other portion of the body part are performed before (I), during (II), and after (III) the reducing of blood flow.

3. Optical detection method according to claim 1, wherein, for the at least one joint and the at least one other portion of the body part, continuous local attenuation measurements are performed before the reducing of blood flow (I), during the reducing of blood flow (II), and after the reducing of blood flow (III).

4. Optical detection method according to claim 1, wherein the blood flow is reduced by application of pressure.

5. Optical detection method according to claim 1, wherein, during the local attenuation measurements, the body part is immersed in a fluid having optical qualities which matches those of the body part.

* * * * *